(12) United States Patent
Lindenbaum et al.

(10) Patent No.: US 7,223,266 B2
(45) Date of Patent: May 29, 2007

(54) METHODS AND APPARATUS FOR HEMOSTASIS FOLLOWING ARTERIAL CATHETERIZATION

(75) Inventors: Hayim Lindenbaum, Haifa (IL); Shimon Eckhouse, Haifa (IL)

(73) Assignee: Cardiodex Ltd., Tirat Hacarmel (IL)

(*) Notice: Subject to any disclaimer, the term of this patent is extended or adjusted under 35 U.S.C. 154(b) by 76 days.

(21) Appl. No.: 10/616,887

(22) Filed: Jul. 10, 2003

(65) Prior Publication Data

US 2004/0153060 A1 Aug. 5, 2004

Related U.S. Application Data

(63) Continuation-in-part of application No. 10/358,130, filed on Feb. 4, 2003, now Pat. No. 7,115,127.

(51) Int. Cl.
*A61B 18/18* (2006.01)

(52) U.S. Cl. .................................. 606/49; 606/213

(58) Field of Classification Search ............ 606/27–52, 606/213

See application file for complete search history.

(56) References Cited

U.S. PATENT DOCUMENTS

| | | | |
|---|---|---|---|
| 3,595,238 A | 7/1971 | Gavrilov et al. | |
| 3,886,944 A | 6/1975 | Jamshidi | |
| 4,202,337 A | 5/1980 | Hren et al. | |
| 4,211,230 A * | 7/1980 | Woltosz ........................ 606/40 |
| 4,364,392 A | 12/1982 | Strother et al. | |
| 4,539,987 A | 9/1985 | Nath et al. | |
| 4,744,364 A | 5/1988 | Kensey | |
| 4,836,204 A | 6/1989 | Landymore et al. | |
| 4,869,248 A | 9/1989 | Narula | |
| 4,929,246 A | 5/1990 | Sinofsky | |
| 5,103,804 A | 4/1992 | Abele et al. | |
| 5,122,137 A | 6/1992 | Lennox | |
| 5,211,624 A | 5/1993 | Cinberg et al. | |
| 5,217,024 A | 6/1993 | Dorsey et al. | |
| 5,342,393 A | 8/1994 | Stack | |
| 5,349,166 A | 9/1994 | Taylor | |
| 5,370,660 A | 12/1994 | Weinstein et al. | |
| 5,383,896 A | 1/1995 | Gershony et al. | |
| 5,413,571 A | 5/1995 | Katsaros et al. | |
| 5,415,657 A | 5/1995 | Taymor-Luria | |
| 5,419,195 A | 5/1995 | Quinn | |

(Continued)

FOREIGN PATENT DOCUMENTS

BR PI0208039 1/2006

(Continued)

OTHER PUBLICATIONS

Overview of CompressAR. 2002.

(Continued)

*Primary Examiner*—Roy D. Gibson
*Assistant Examiner*—Pete Vrettakos
(74) *Attorney, Agent, or Firm*—Patton Boggs

(57) ABSTRACT

A method for producing hemostasis of an artery of a patient having a puncture following arterial catheterization including introducing a hemostasis device including at least one electrode into the vicinity of the puncture, supplying an electric current to the at least one electrode, thereby heating blood in the vicinity of the puncture and causing coagulation of the blood and subsequently removing the hemostasis device from the patient.

11 Claims, 11 Drawing Sheets

U.S. PATENT DOCUMENTS

| | | | |
|---|---|---|---|
| 5,419,765 A | 5/1995 | Weldon et al. | |
| 5,458,573 A | 10/1995 | Summers | |
| 5,486,195 A * | 1/1996 | Myers et al. | 606/213 |
| 5,507,744 A * | 4/1996 | Tay et al. | 606/50 |
| 5,540,715 A | 7/1996 | Katsaros et al. | |
| 5,626,601 A | 5/1997 | Gershony et al. | |
| 5,645,566 A | 7/1997 | Brenneman et al. | |
| 5,700,277 A | 12/1997 | Nash et al. | |
| 5,716,375 A | 2/1998 | Fowler | |
| 5,725,551 A | 3/1998 | Myers et al. | |
| 5,728,133 A | 3/1998 | Kontos | |
| 5,728,134 A | 3/1998 | Barak | |
| 5,782,860 A | 7/1998 | Epstein et al. | |
| 5,810,810 A | 9/1998 | Tay et al. | |
| 5,853,421 A | 12/1998 | Leschinsky et al. | |
| 5,868,778 A | 2/1999 | Gershony et al. | |
| 5,879,499 A | 3/1999 | Corvi | |
| 5,891,138 A | 4/1999 | Tu et al. | |
| 5,895,386 A | 4/1999 | Odell et al. | |
| 5,922,009 A | 7/1999 | Epstein et al. | |
| 5,928,266 A * | 7/1999 | Kontos | 606/213 |
| 5,941,897 A | 8/1999 | Myers | |
| 6,022,336 A | 2/2000 | Zadno-Azizi et al. | |
| 6,033,398 A | 3/2000 | Farley et al. | |
| 6,033,401 A | 3/2000 | Edwards et al. | |
| 6,048,358 A | 4/2000 | Barak | |
| 6,056,768 A | 5/2000 | Cates et al. | |
| 6,063,085 A | 5/2000 | Tay et al. | |
| 6,071,277 A | 6/2000 | Farley et al. | |
| 6,113,598 A | 9/2000 | Baker | |
| 6,126,635 A | 10/2000 | Simpson et al. | |
| 6,142,994 A | 11/2000 | Swanson et al. | |
| 6,152,920 A | 11/2000 | Thompson et al. | |
| 6,179,832 B1 | 1/2001 | Jones et al. | |
| 6,228,082 B1 | 5/2001 | Baker et al. | |
| 6,235,027 B1 | 5/2001 | Herzon | |
| 6,322,559 B1 | 11/2001 | Daulton et al. | |
| 6,352,533 B1 | 3/2002 | Ellman et al. | |
| 6,398,780 B1 | 6/2002 | Farley et al. | |
| 6,398,782 B1 | 6/2002 | Pecor et al. | |
| 6,402,745 B1 | 6/2002 | Wilk | |
| 6,443,947 B1 | 9/2002 | Marko et al. | |
| 6,450,989 B2 * | 9/2002 | Dubrul et al. | 604/104 |
| 6,451,007 B1 | 9/2002 | Koop et al. | |
| 6,503,247 B2 * | 1/2003 | Swartz et al. | 606/41 |
| 6,533,778 B2 | 3/2003 | Herzon | |
| 6,846,321 B2 | 1/2005 | Zucker | |
| 7,008,441 B2 | 3/2006 | Zucker | |
| 7,115,127 B2 | 10/2006 | Lindenbaum et al. | |
| 2001/0029373 A1 | 10/2001 | Baker et al. | |
| 2002/0072761 A1 | 6/2002 | Abrams et al. | |
| 2002/0156495 A1 | 10/2002 | Brenneman et al. | |
| 2002/0193808 A1 | 12/2002 | Belef et al. | |
| 2003/0055397 A1 | 3/2003 | Zucker | |
| 2003/0093116 A1 | 5/2003 | Nowakowski | |
| 2003/0109869 A1 | 6/2003 | Shadduck | |
| 2003/0120256 A1 | 6/2003 | Lary et al. | |
| 2003/0125766 A1 | 7/2003 | Ding | |
| 2003/0153060 A1 | 8/2003 | Wilson et al. | |
| 2003/0199863 A1 | 10/2003 | Swanson et al. | |
| 2003/0236518 A1 | 12/2003 | Marchitto et al. | |
| 2004/0010298 A1 | 1/2004 | Altshuler et al. | |
| 2004/0092913 A1 | 5/2004 | Hennings et al. | |
| 2004/0199155 A1 | 10/2004 | Mollenauer | |
| 2004/0249342 A1 | 12/2004 | Khosravi et al. | |
| 2006/0235376 A1 | 10/2006 | Lindenbaum et al. | |

FOREIGN PATENT DOCUMENTS

| | | |
|---|---|---|
| CA | 2514865 | 8/2004 |
| DK | 1096884 T | 8/2006 |
| EP | 1096884 | 5/2001 |
| EP | 1599239 | 11/2005 |
| EP | 1711117 | 10/2006 |
| JP | 2006-502628 | 1/2006 |
| WO | WO 98/11830 | 3/1998 |
| WO | WO-9811830 | 3/1998 |
| WO | WO 00/02488 | 1/2000 |
| WO | WO-0002488 | 1/2000 |
| WO | WO 02/072188 | 9/2002 |
| WO | WO-02072188 | 9/2002 |
| WO | WO-04069300 | 11/2005 |
| WO | WO-06/054170 | 5/2006 |
| WO | WO-05074364 | 5/2006 |
| WO | WO-06054170 | 5/2006 |

OTHER PUBLICATIONS

Angio-Seal™. 2002.
The Prostar®, Perclose, Inc. 2002.
Silber, S. "Vascular Closure Devices for Immediate..", in Handbook of Coronary Stents, 3$^{rd}$ ed. (Martin Dunitz, 2000).
U.S. Appl. No. 10/543,654, filed Jul. 10, 2005, Eckhouse et al.
U.S. Appl. No. 60/630,245, Eckhouse et al.

* cited by examiner

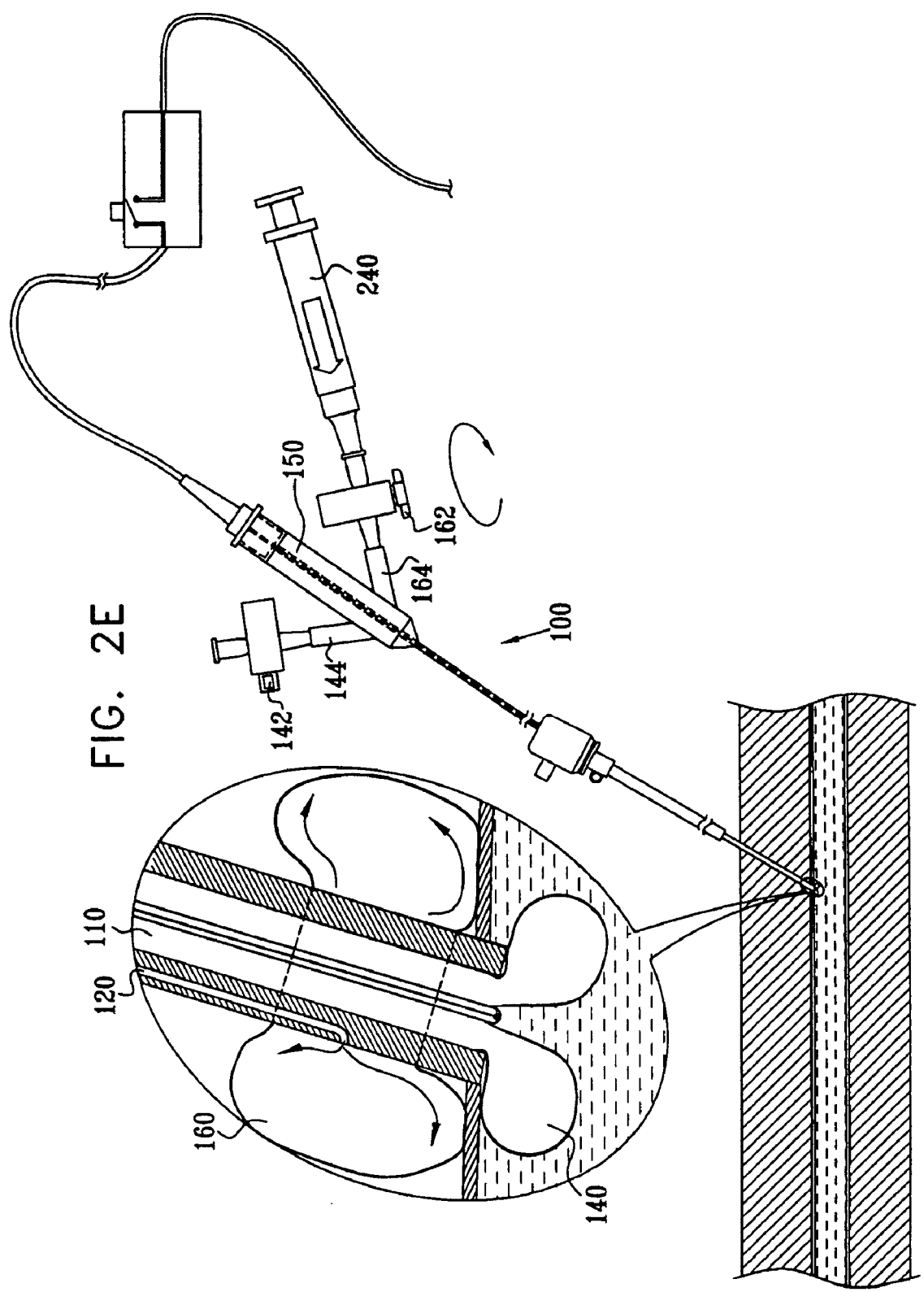

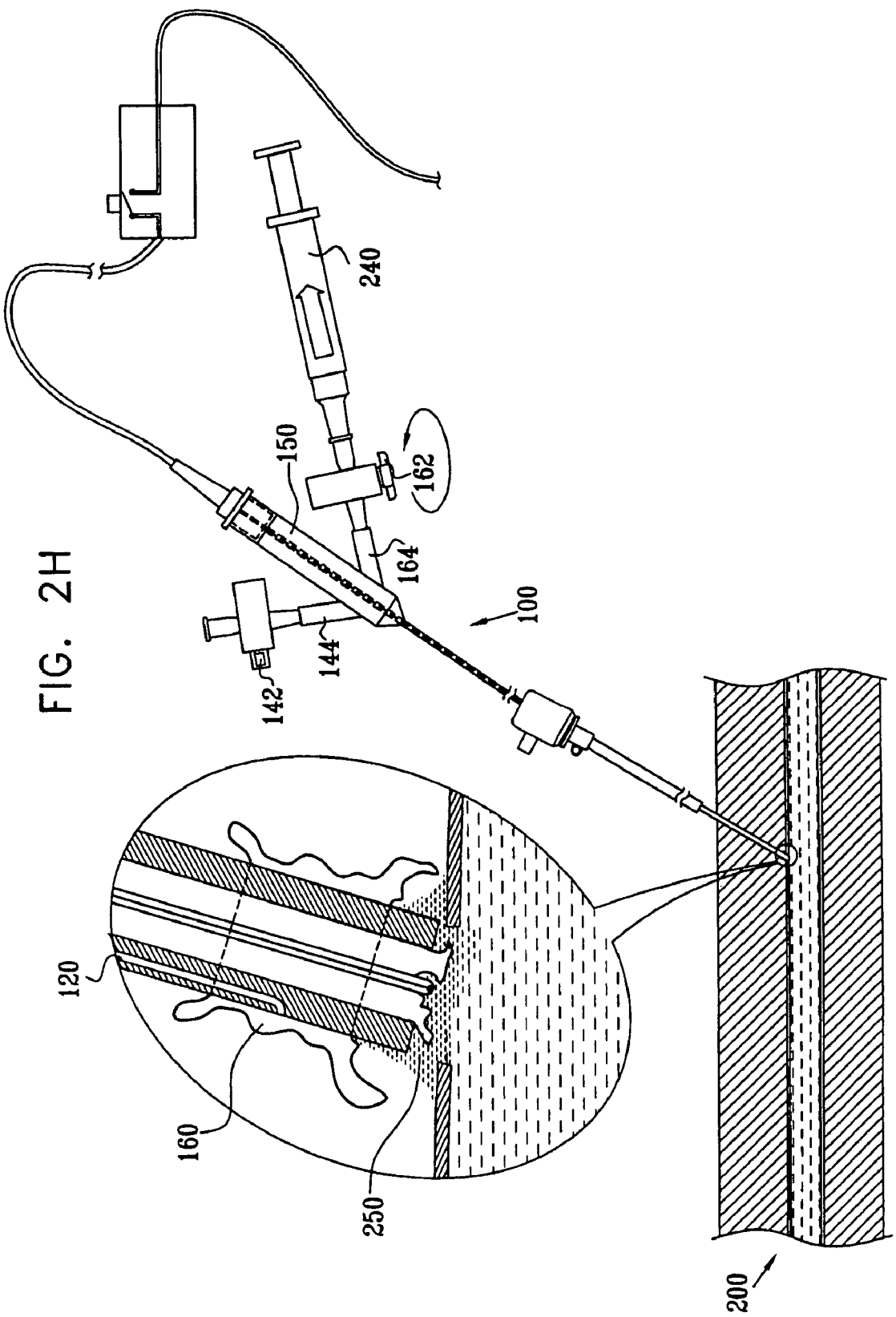

METHODS AND APPARATUS FOR HEMOSTASIS FOLLOWING ARTERIAL CATHETERIZATION

CROSS REFERENCE TO RELATED APPLICATIONS

This application is a continuation-in-part of U.S. application Ser. No. 10/358,130, filed Feb. 4, 2003 now U.S. Pat. No. 7,115,127, titled "METHODS AND APPARATUS FOR HEMOSTASIS FOLLOWING ARTERIAL CATHETERIZATION", the contents of which are incorporated by reference.

FIELD OF THE INVENTION

The present invention relates to catheterization systems and methodologies generally and more particularly to post-catheterization closure.

BACKGROUND OF THE INVENTION

Various techniques are known for arterial catheterization. Following arterial catheterization, it is necessary to promote hemostasis quickly and without undue hardship for the patient.

Applicant's U.S. Pat. Nos. 5,728,134 and 6,048,358, and Published PCT Patent Applications WO 98/11830 and WO 00/02488 describe methods and apparatus for hemostasis that greatly simplifies hemostasis and thus greatly reduces patient discomfort following arterial catheterization. These patent documents, the disclosures of which are hereby incorporated by reference, and the prior art referenced therein are considered to represent the state of the art.

SUMMARY OF THE INVENTION

The present invention seeks to provide improved systems and methodologies for post-catheterization closure.

There is thus provided in accordance with a preferred embodiment of the present invention a method for producing hemostasis of an artery of a patient having a puncture following arterial catheterization including introducing a hemostasis device including at least one electrode into the vicinity of the puncture, supplying an electric current to the at least one electrode, thereby heating a volume of blood in the vicinity of the puncture, causing coagulation of the blood and causing closure of the puncture and subsequently removing the hemostasis device from the patient.

In accordance with another preferred embodiment of the present invention the at least one electrode includes a pair of electrodes.

In accordance with yet another preferred embodiment of the present invention the introducing includes introducing via a catheter introducer. Additionally, the introducing also includes inflating an anchor balloon attached to an end of the hemostasis device. Alternatively or additionally, the introducing also includes inflating a peripheral balloon. In accordance with still another preferred embodiment of the present invention the removing the hemostasis device includes deflating the peripheral balloon.

In accordance with another preferred embodiment of the present invention the introducing also includes positioning the at least one electrode in close proximity to the volume of blood.

Preferably, the supplying includes supplying electrical power at RF frequencies. Additionally, the electrical power includes electrical power in the range of 0.1–10 watts at up to 25 volts.

In accordance with yet another preferred embodiment of the present invention the supplying also includes adjusting the electric current based on a feedback measurement.

There is also provided in accordance with another preferred embodiment of the present invention a hemostasis device including a main shaft, at least one balloon and at least one electrode, operable to supply an electric current and to thereby heat a volume of blood adjacent to the at least one electrode and to cause coagulation of the blood and closure of the puncture.

In accordance with another preferred embodiment of the present invention the at least one balloon includes at least one anchor balloon, disposed at an end of the main shaft and at least one peripheral balloon, disposed at a location along the main shaft exterior to a wall of the main shaft. Preferably, the volume of blood is delimited by the peripheral balloon and a wall of the artery.

In accordance with yet another preferred embodiment of the present invention the hemostasis device also includes an electrical power source and control module. Additionally, the electrical power source and control module includes a power supply, operative to supply power to the at least one electrode, feedback measurement means and a processor.

Preferably, the power supply includes an RF power supply which supplies electrical power at RF frequencies within a range of 0.1–10 watts at up to 25 volts.

In accordance with still another preferred embodiment of the present invention the feedback measurement means is operative to measure at least one of electrical current, blood resistance and blood temperature.

Additionally, the processor is operative to adjust the power based on an output from the feedback measurement means.

In accordance with yet another preferred embodiment of the present invention the at least one electrode includes a pair of electrodes.

There is further provided in accordance with yet another preferred embodiment of the present invention a method for producing hemostasis of an artery of a patient having a puncture following arterial catheterization, including introducing a hemostasis device including at least one electrode into the vicinity of the puncture, positioning the at least one electrode in proximity with the puncture, supplying an electric current to the at least one electrode, thereby heating a volume of blood in the vicinity of the puncture, causing coagulation of the blood and causing closure of the puncture and subsequently removing the hemostasis device from the patient.

In accordance with another preferred embodiment of the present invention the positioning includes inflating an anchor balloon attached to an end of the hemostasis device, inflating a peripheral balloon and subsequently deflating the anchor balloon. Preferably, the volume of blood is delimited by the peripheral balloon and a wall of the artery.

In accordance with still another preferred embodiment of the present invention the at least one electrode includes a pair of electrodes.

In accordance with yet another preferred embodiment of the present invention the supplying includes supplying electrical power at RF frequencies. Additionally, the electrical power includes electrical power in the range of 0.1–10 watts at up to 25 volts.

In accordance with another preferred embodiment of the present invention the supplying also includes adjusting the electric power based on a feedback measurement.

BRIEF DESCRIPTION OF THE DRAWINGS

The present invention will be understood and appreciated more fully from the following detailed description, taken in conjunction with the drawings in which:

FIGS. 2A, 2B, 2C, 2D, 2E, 2F, 2G, 2H and 2I are simplified illustrations of the operation of the apparatus of FIG. 1 in a patient treatment context.

DETAILED DESCRIPTION OF PREFERRED EMBODIMENTS

Figure 1:
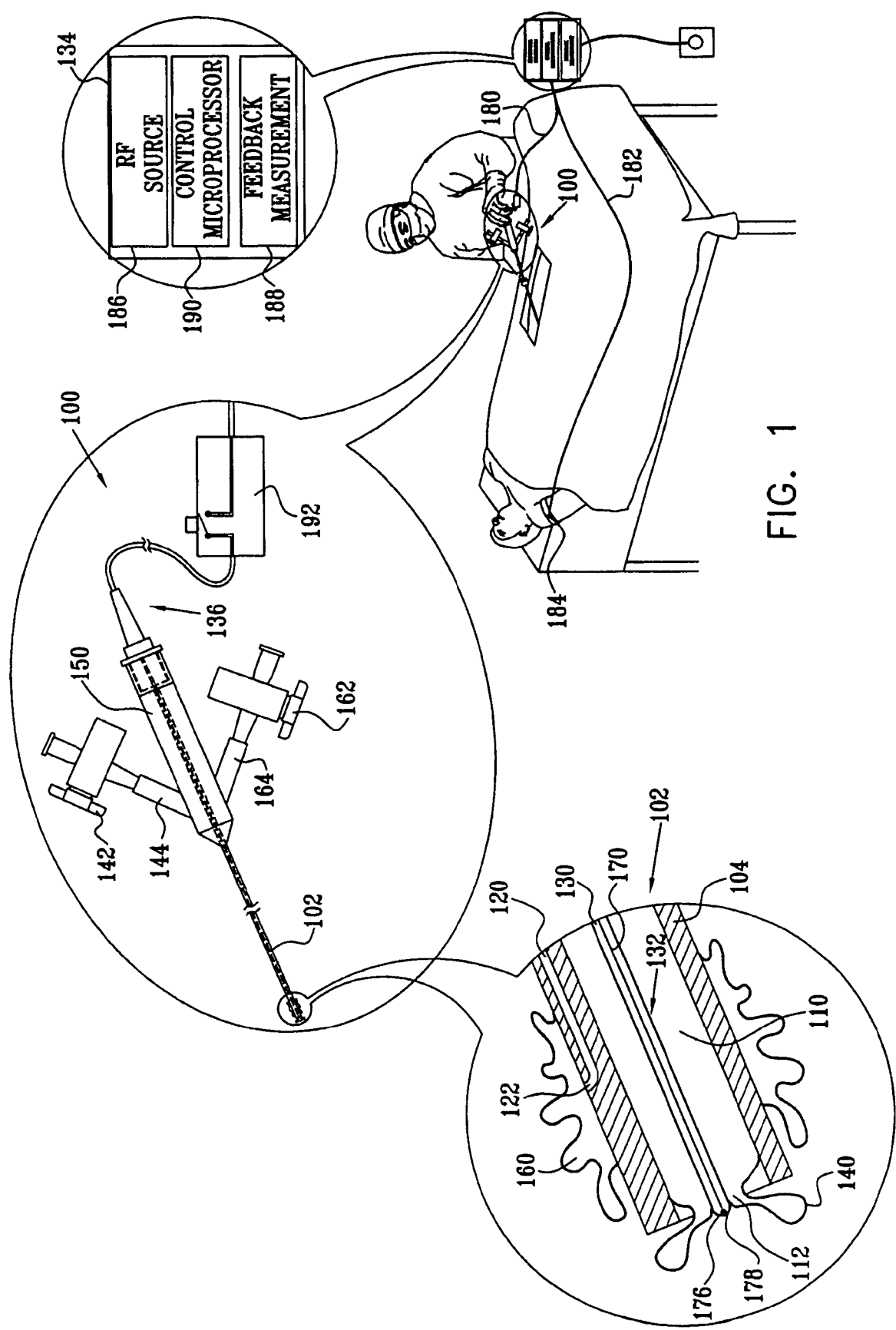
FIG. 1 is a simplified illustration of a hemostasis device constructed and operative in accordance with a preferred embodiment of the present invention.

Reference is now made to FIG. 1, which is a simplified illustration of a hemostasis device 100 for producing hemostasis following arterial catheterization, in accordance with a preferred embodiment of the present invention. The hemostasis device 100 is suitable for insertion via a conventional catheter introducer (not shown) following completion of catheterization and removal of the catheter from the catheter introducer.

In accordance with a preferred embodiment of the present invention, hemostasis device 100 comprises a main shaft 102, which has an outer wall 104 and preferably includes at least three bores. A first bore, designated generally by reference numeral 110, extends along the main shaft 102 to an anchor balloon inflation location 112. A second bore 120 extends along the shaft 102 to a peripheral balloon inflation location 122. A third bore, designated generally by reference number 130, contains an electrocoagulation heating device 132 connected to an electrical power source and control module 134 by a connector 136.

Disposed at an end of main shaft 102 at anchor balloon inflation location 112 is an anchor balloon 140. Anchor balloon 140 is selectably inflated, as shown in FIG. 2C, via a stopcock 142 and associated conduit 144 in fluid communication with main shaft 102 via a head element 150. Head element 150 is fixed to main shaft 102 at an end thereof opposite the end at which anchor balloon 140 is located. The interior of head element 150 is in fluid communication with first bore 110 in main shaft 102, which in turn is in fluid communication with the interior of the anchor balloon 140 at anchor balloon inflation location 112.

Disposed adjacent the end of second bore 120 in fluid communication with peripheral balloon inflation location 122, exterior of wall 104, is a peripheral balloon 160. Peripheral balloon 160 is selectably inflated, as shown in FIG. 2E, via second bore 120, via a stopcock 162 and associated conduit 164 that communicate with second bore 120 via head element 150.

In accordance with a preferred embodiment of the present invention, electrocoagulation heating device 132 comprises an electrical conductor 170 connected to an electrocoagulation electrode 176 at an extreme end 178 of third bore 130. A pair of electrical cables 180 and 182 extend from electrical power source and control module 134. In the illustrated embodiment, electrical cable 180 serves as a power supply cable and is connected to electrocoagulation heating device 132 by connector 136. Electrical cable 182 serves as a return current cable and is preferably connected to an electrode 184 attached to a body of a patient.

Electrical power source and control module 134 preferably comprises a power supply, preferably an RF power supply source 186, including a feedback measurement circuit 188. The feedback measurement circuit 188 is preferably operative to measure current, blood resistance or blood temperature and thereby determine progress of hemostasis. The electrical power source and control module 134 also preferably includes a microprocessor 190, operative to adjust the power supplied to hemostasis device 100 according to the blood temperature or other feedback measurement received from feedback measurement circuit 188, in order to achieve optimal coagulation of the blood.

In accordance with a preferred embodiment of the present invention an operator actuation switch 192 is connected along electrical cable 180. In accordance with another preferred embodiment, switch 192 may be obviated and electrical cable 180 connected directly to connector 136.

Reference is now made to FIGS. 2A–2I, which illustrate various steps in a preferred mode of operation of the apparatus of FIG. 1.

Figure 2A:
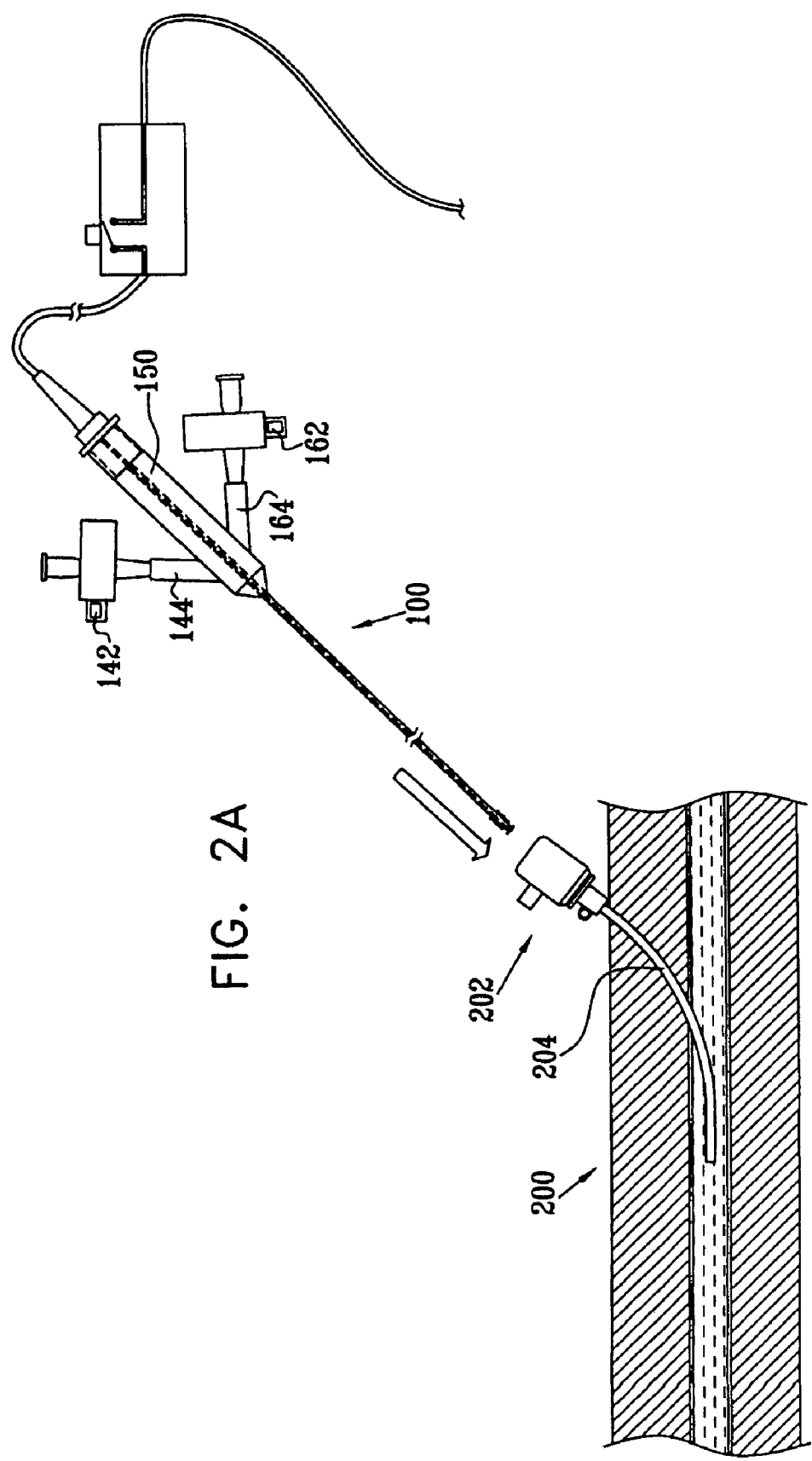

FIG. 2A illustrates the hemostasis device 100 about to be inserted into an artery 200 via a conventional catheter introducer assembly 202, following completion of a catheterization procedure and withdrawal of a catheter (not shown) from the catheter introducer assembly 202. The catheter introducer assembly 202 conventionally includes a catheter introducer sheath 204.

Figure 2B:
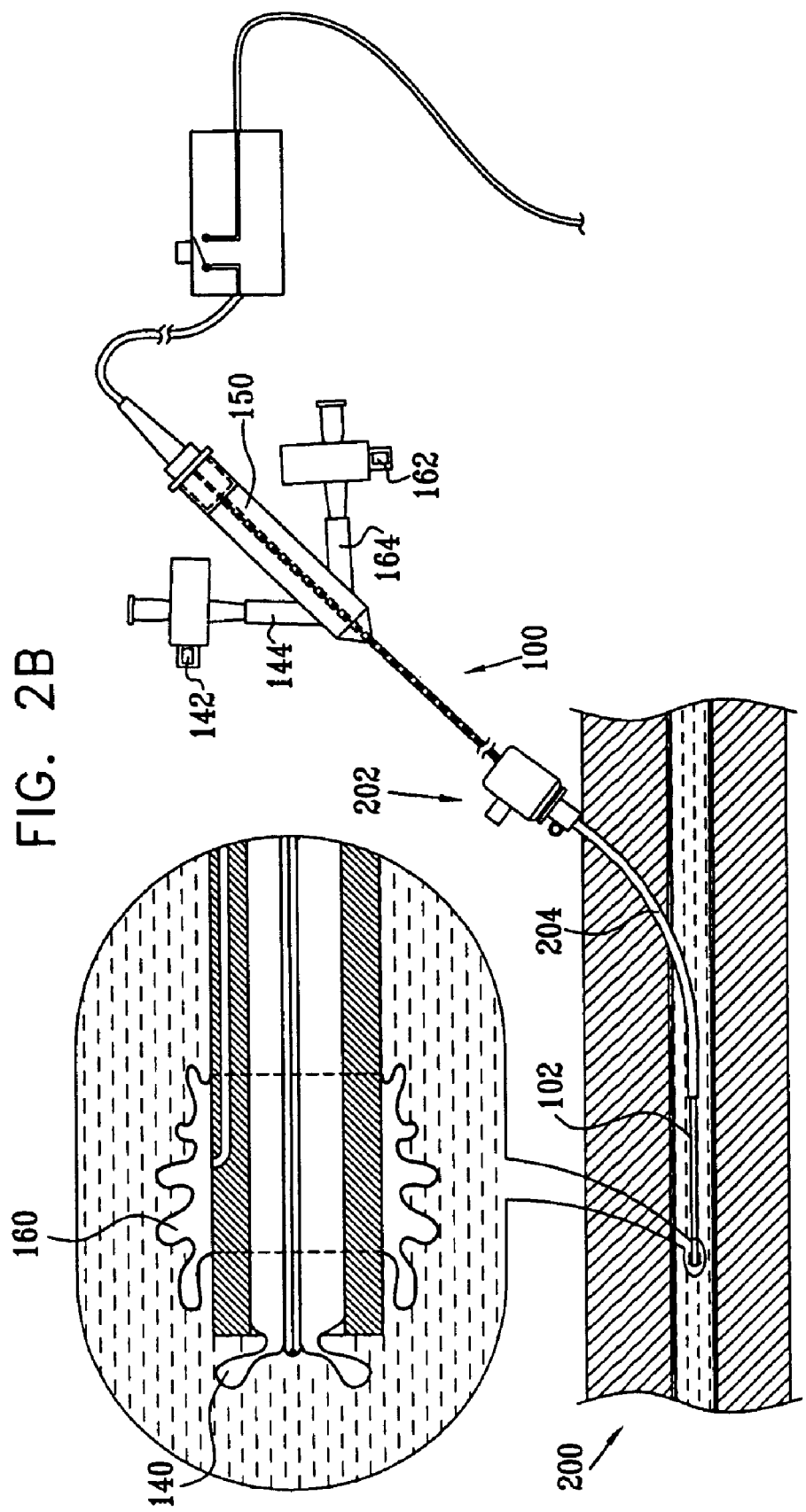
Figure 2C:
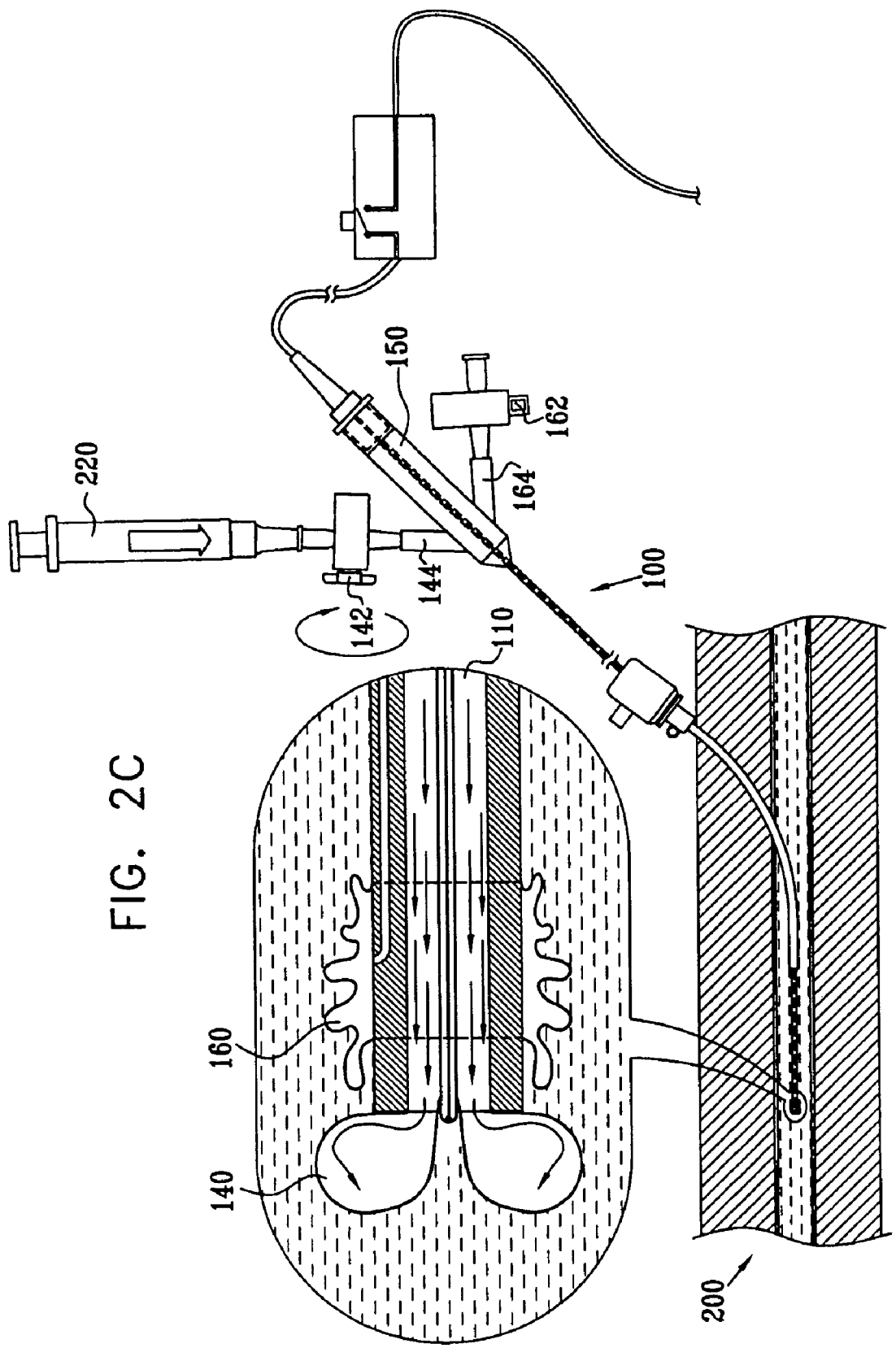

FIG. 2B shows the hemostasis device 100 inserted into the catheter introducer assembly 202 such that the outer end of the main shaft 102 extends into the artery 200 well beyond the end of catheter introducer sheath 204. As shown with particularity in FIG. 2B, at this stage both anchor balloon 140 and peripheral balloon 160 are deflated.

Reference is now made to FIG. 2C, which shows initial inflation of the anchor balloon 140, preferably by use of a syringe 220 communicating with first bore 110 via the interior of head element 150, stopcock 142 and associated conduit 144. The inflated anchor balloon 140 preferably has a cusp-type configuration as seen with particularity in FIG. 2C.

Figure 2D:
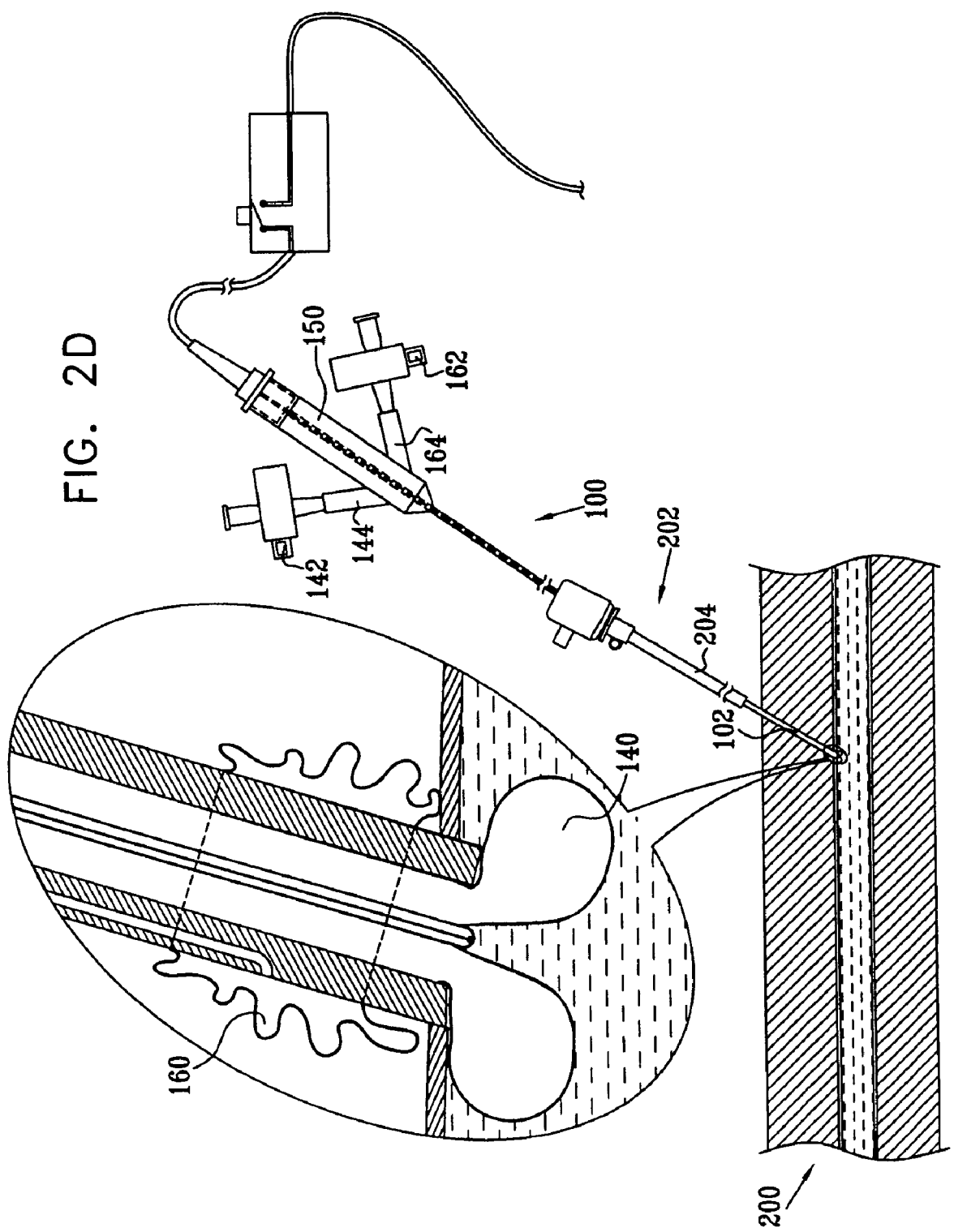

Following inflation of the anchor balloon 140, the catheter introducer assembly 202 and the hemostasis device 100 are both withdrawn, such that the catheter introducer sheath 204 is removed from artery 200 only when the anchor balloon 140 already engages the interior wall of artery 200 in sealing engagement with the aperture in the artery 200 through which the catheter introducer sheath 204 is drawn and through which the main shaft 102 presently extends. This stage is shown in FIG. 2D.

As seen in FIG. 2E, initial inflation of the peripheral balloon 160 is effected, preferably by use of a syringe 240 communicating with second bore 120 via head element 150, stopcock 162 and associated conduit 164.

Figure 2F:
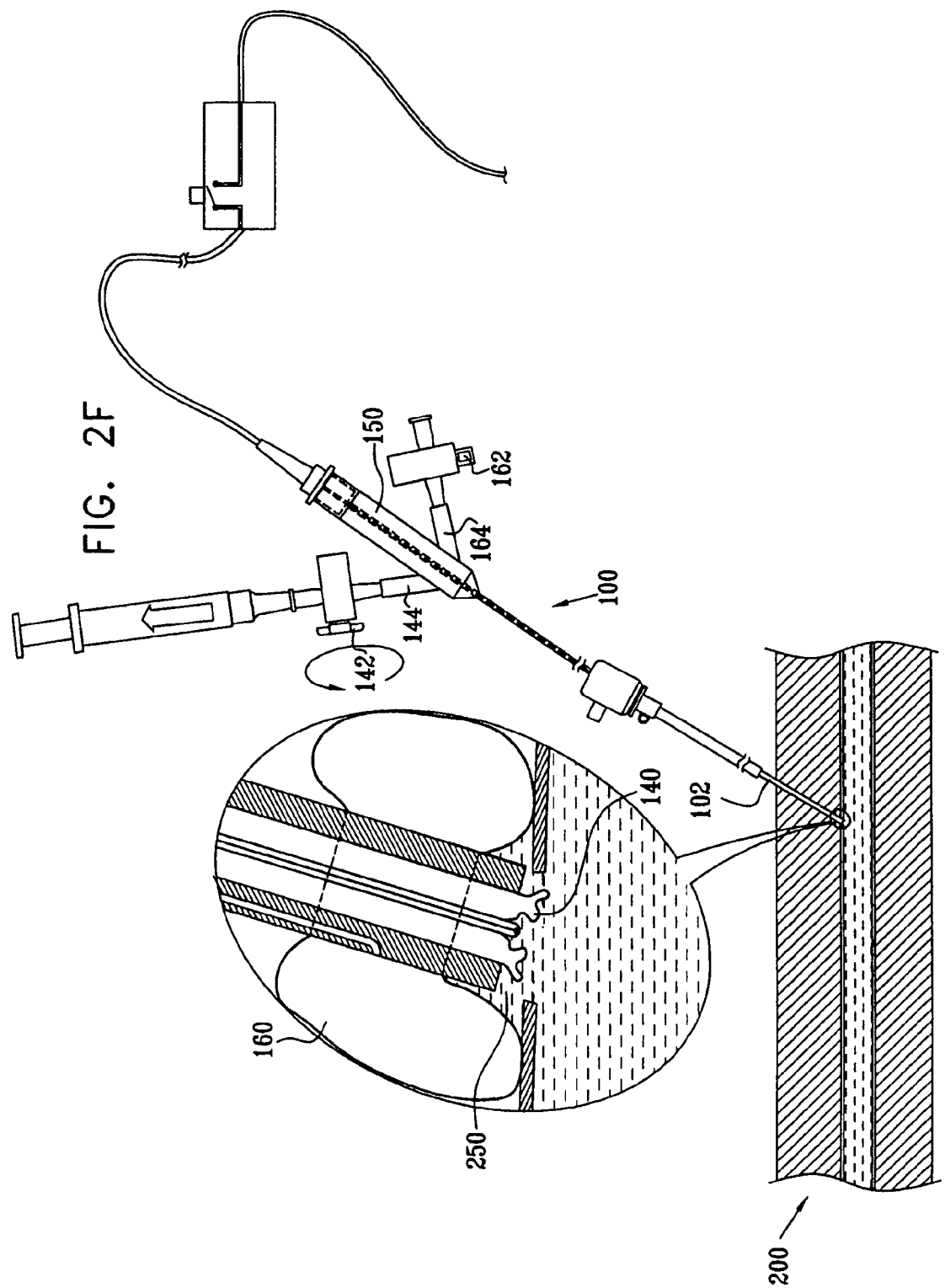

Thereafter, as seen in FIG. 2F, the anchor balloon 140 is deflated and the peripheral balloon 160 is more fully inflated, which preferably causes the extreme end of the main shaft 102 to be withdrawn from the artery 200 to a location lying just outside the artery wall. As seen in FIG. 2F, peripheral balloon 160 is preferably designed to allow a limited volume of blood to collect outside of the artery wall after the anchor balloon 140 is deflated. This volume of blood is located in a region, indicated by reference numeral 250, delimited by the engagement of peripheral balloon 160 with the artery wall.

Figure 2G:
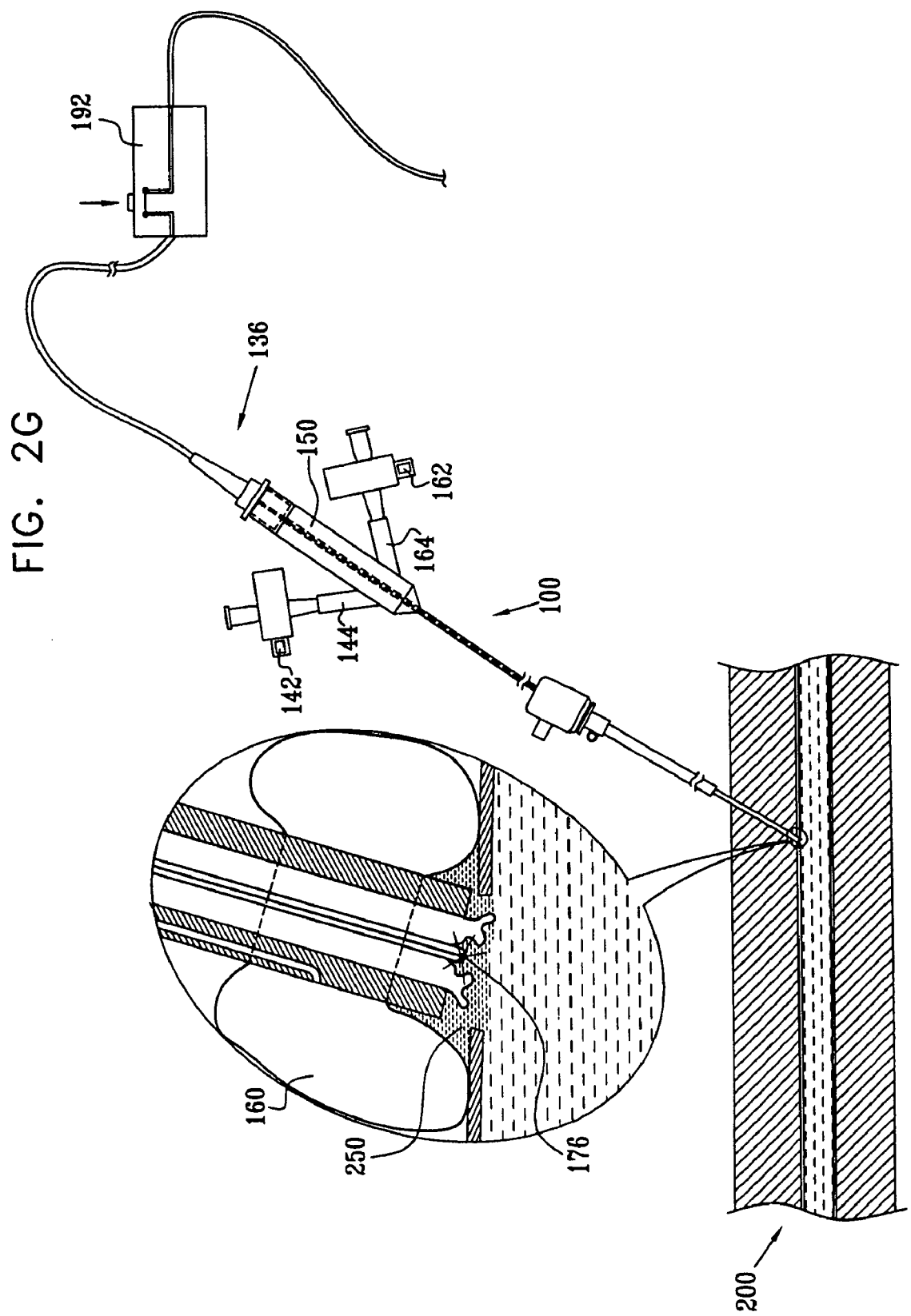

At this stage, electric power is supplied to the electrode 176 to provide heating of the blood in region 250, causing coagulation thereof, as seen in FIG. 2G. In accordance with the illustrated embodiment of FIG. 1 and as shown in FIG. 2G, the electric power is provided by actuation of switch 192. In accordance with another preferred embodiment, switch 192 is obviated, and the electric power is provided by connecting electrical cable 180 (FIG. 1) directly to connector 136.

Preferably, the amount of electrical power supplied along electrical cable 180 (FIG. 1) from electrical power source and control module 134 to the electrocoagulation electrode 176 is between 0.1–10 watts at up to 25 volts at RF frequencies.

Once acceptable hemostasis has occurred in region 250, the peripheral balloon 160 is deflated, as shown in FIG. 2H, preferably by operation of syringe 240 communicating with second bore 120 via head element 150, stopcock 162 and associated conduit 164.

Figure 2I:
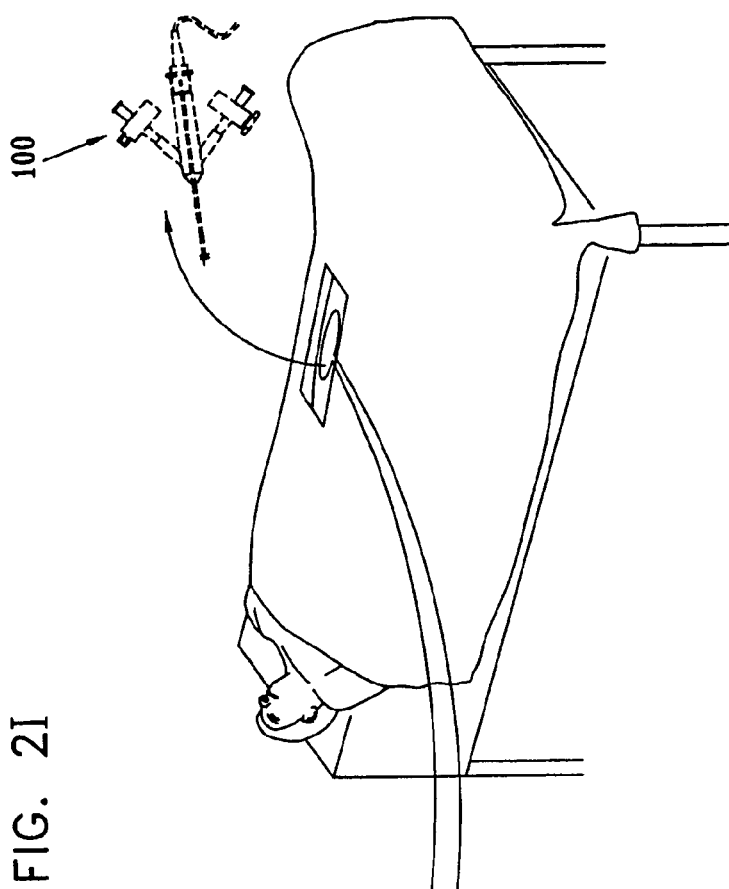
Figure 2I:
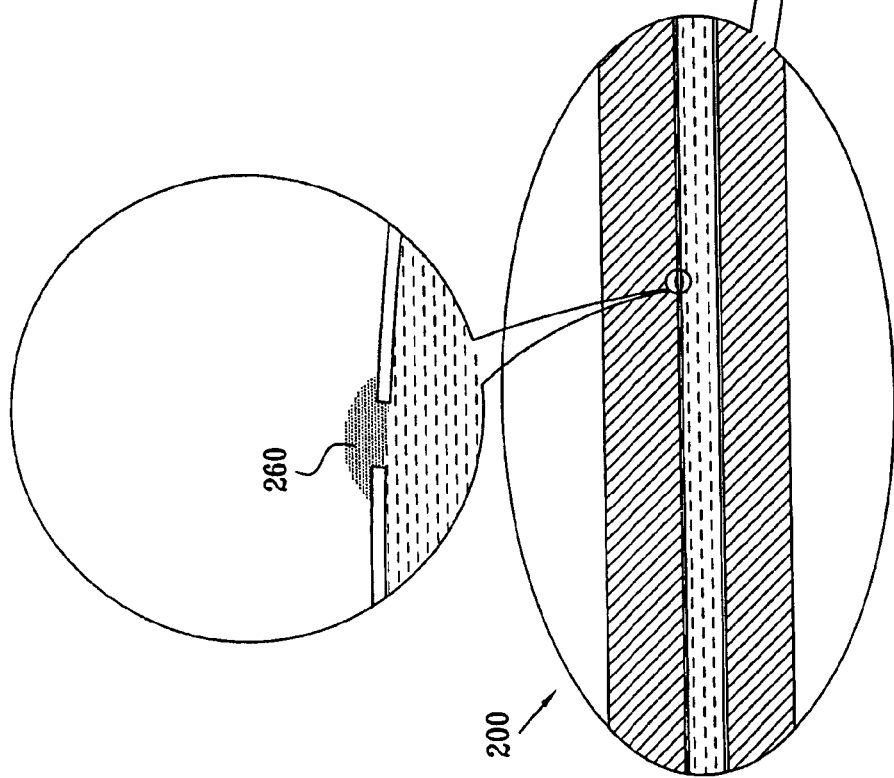

Thereafter, the hemostasis device 100 is entirely withdrawn from the patient, leaving a region 260 of hemostasis outside of artery 200, as shown in FIG. 2I.

Figure 3:
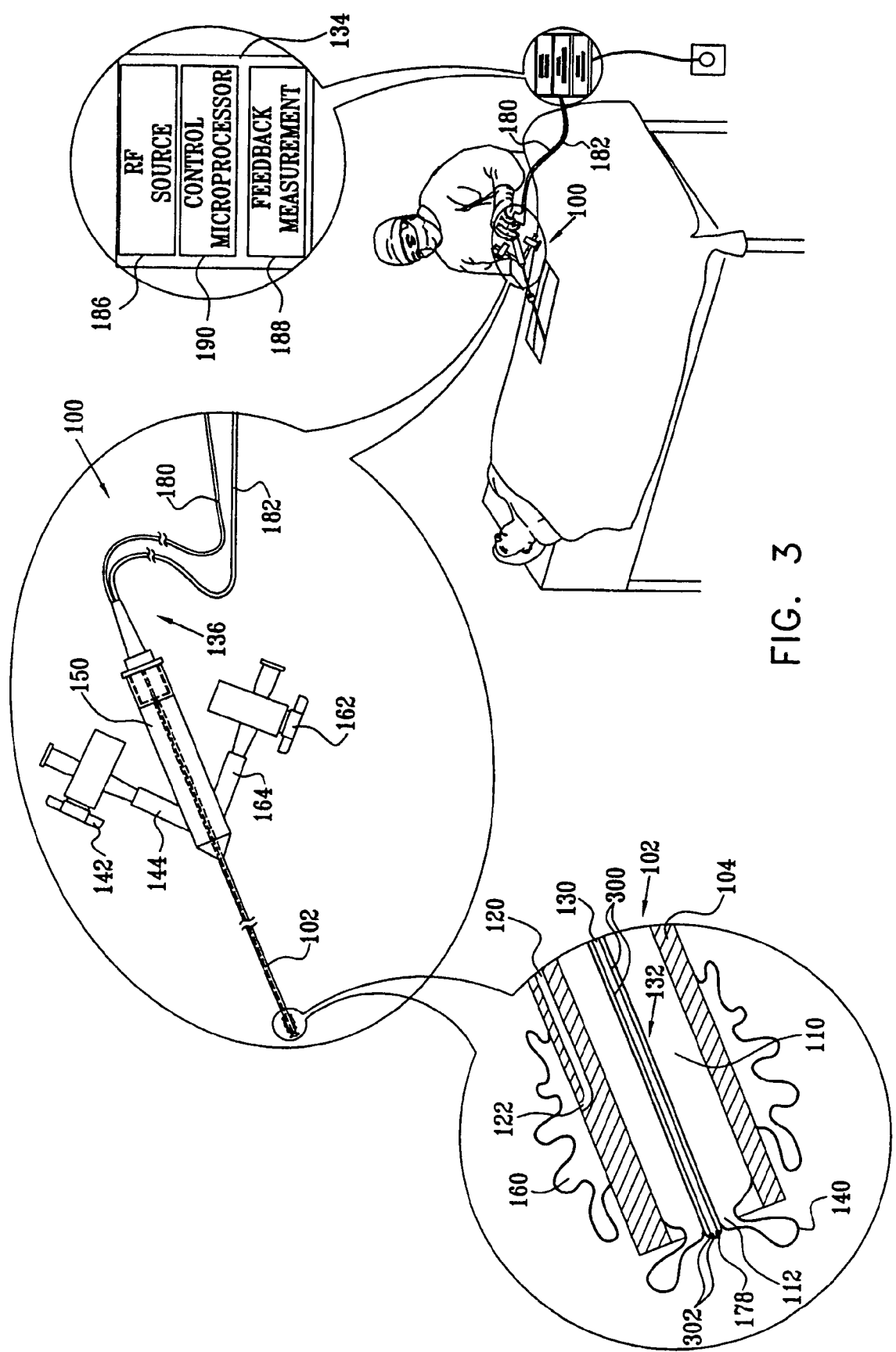
FIG. 3 is a simplified illustration of a hemostasis device constructed and operative in accordance with another preferred embodiment of the present invention.

Reference is now made to FIG. 3, which is a simplified illustration of a hemostasis device constructed and operative in accordance with another preferred embodiment of the present invention. The embodiment of FIG. 3 is similar to that of FIG. 1, except as described hereinbelow. Elements that occur in both embodiments are identified by the same reference numerals.

In the embodiment of FIG. 3, electrocoagulation heating device 132 comprises a pair of separate electrical conductors 300 extending along third bore 130 connecting electrical power source and control module 134 to a pair of electrocoagulation electrodes 302 at end 178 of third bore 130. Electrical cables 180 and 182 are both connected to electrocoagulation heating device 132 by connector 136. The illustrated embodiment shows connector 136 directly connected to electrical cables 180 and 182.

In the embodiment of FIG. 3, the electrodes 302 may be arranged in mutual coaxial arrangement or in mutual side-by-side arrangement or any other suitable arrangement.

It will be appreciated by persons skilled in the art that the present invention is not limited by what has been particularly shown and described hereinabove. Rather the scope of the present invention includes both combinations and subcombinations of the various features described hereinabove and shown in the drawings as well as modifications and further developments thereof which would occur to a person of ordinary skill in the art upon reading the foregoing description and which are not in the prior art.

The invention claimed is:

1. A hemostasis device for closing a puncture in an artery wall, comprising:
   a main shaft;
   at least one expandable member disposed on the main shaft, wherein the expandable member in one configuration is adapted to delimit a blood coagulation volume by the engagement of the expandable member against an outside of an artery wall; and
   at least one electrode, operable to supply an electric current, coupled to the main shaft in the vicinity of the blood coagulation volume, wherein upon activation of the electrode, the electrode is adapted to cause blood disposed in the blood coagulation volume to coagulate thereby causing a closure of the puncture.

2. A hemostasis device according to claim 1 and wherein the at least one expandable member comprises: at least one anchor balloon, disposed at an end of the main shaft; and at least one peripheral balloon, disposed at a location along the main shaft exterior to a wall of the main shaft.

3. A hemostasis device according to claim 2 and wherein the blood coagulation volume is delimited by the peripheral balloon and the artery wall.

4. A hemostasis device according to claim 1 and also comprising an electrical power source and control module connected to the electrode.

5. A hemostasis device according to claim 4 and wherein the electrical power source and control module comprises: a power supply, operative to supply power to the at least one electrode; feedback measurement means for supplying feedback measurements; and a processor.

6. A hemostasis device according to claim 5 and wherein the power supply is an RF power supply.

7. A hemostasis device according to claim 6 and wherein the RF power supply is operative to supply electrical power at RF frequencies within a range of 0.1–10 watts at up to 25 volts.

8. A hemostasis device according to claim 5 and wherein the feedback measurement means is operative to measure at least one of electrical current, blood resistance end blood temperature.

9. A hemostasis device according to claim 5 and wherein the processor is operative to adjust the power based on an output from the feedback measurement means.

10. A hemostasis device according to claim 1 and wherein the at least one electrode is disposed at a distal end of the device.

11. A hemostasis device according to claim 1, where the electrode is disposed at a distal tip of the main shaft.

\* \* \* \* \*